US008465427B1

(12) United States Patent  
Qin

(10) Patent No.: US 8,465,427 B1
(45) Date of Patent: Jun. 18, 2013

(54) COMBINED DIAGNOSTIC CONFOCAL SCANNING AND LOW INTENSITY ULTRASOUND TREATMENT

(75) Inventor: Yi-Xian Qin, Port Jefferson Station, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/727,996

(22) Filed: Mar. 19, 2010

Related U.S. Application Data

(63) Continuation-in-part of application No. 12/297,079, filed on Oct. 14, 2008.

(60) Provisional application No. 61/161,574, filed on Mar. 19, 2009.

(51) Int. Cl.
*A61B 8/00* (2006.01)
*G01H 15/00* (2006.01)
*A61H 1/00* (2006.01)

(52) U.S. Cl.
USPC ............... 600/438; 600/449; 73/597; 73/599; 601/2

(58) Field of Classification Search
USPC .................. 600/437–472; 73/597, 599; 601/2
See application file for complete search history.

(56) References Cited

U.S. PATENT DOCUMENTS

| 5,103,806 A | * | 4/1992 | McLeod et al. | 601/2 |
| 7,727,152 B2 | * | 6/2010 | Qin et al. | 600/449 |
| 2008/0021327 A1 | * | 1/2008 | El-Bialy et al. | 600/459 |

OTHER PUBLICATIONS

Chen PJ, Chen T, Lu MC, Yao WJ. The measurements of ultrasound parameters on calcaneus by two-sided interrogation techniques. Meas. Sci. Technol. 2005;16:1349-1354.*

* cited by examiner

*Primary Examiner* — Michael Rozanski
(74) *Attorney, Agent, or Firm* — Scully, Scott, Murphy & Presser, P.C.

(57) ABSTRACT

Disclosed is a method and apparatus for non-invasive bone fracture detection and accelerated healing, that simultaneously maps, via a paired phased array ultrasound scanning apparatus having multi-element transducers, three dimensional bone surface topology at opposite surfaces along an ultrasound wave pathway; that measures, using the mapped three dimensional topology, a thickness of the mapped bone; that detects, using the mapped three dimensional topology, a region of interest with bone deterioration or fracture; that calculates an ultrasonic wave velocity and attenuation as the ultrasound wave passes through the detected region of interest; and that applies a low-intensity pulsed ultrasound (LIPUS) pulse to the region of interest. The paired phased array ultrasound scanning apparatus focuses the application of the LIPUS pulse.

18 Claims, 2 Drawing Sheets

COMBINED DIAGNOSTIC CONFOCAL SCANNING AND LOW INTENSITY ULTRASOUND TREATMENT

PRIORITY

This application claims priority to U.S. Provisional Patent Application No. 61/161,574, filed Mar. 19, 2009, and to U.S. patent application Ser. No. 12/297,079, filed Oct. 14, 2008, the contents of each of which are incorporated herein by reference.

BACKGROUND OF THE INVENTION

1. Field of the Invention

Ultrasound imaging is utilized for real-time, noninvasive, nondestructive assessment of material density and strength of hard tissue to determine complex three-dimensional shapes, surface topology, non-uniform internal structures and to determine material properties of tissues.

The present invention combines a Low Intensity Pulsed Ultrasound (LIPUS) device with a surface topology mapping apparatus to provide focused ultrasound therapy to enhance healing and accelerate callus mineralization.

2. Brief Description of the Background Art

Osteoporosis and osteopenia are common diseases affecting a large proportion of the population, mostly elderly, which increase the risk of fracture at critical skeletal sites, e.g., hip, wrist and spine. After fracture, healing complications include non-union and poor quality of life. Various remedies have been developed to treat delayed unions and non-unions.

Ultrasound (US) is known to have a strong positive influence on the three key stages of the healing process: inflammation, repair, and remodeling, due to the enhancement by US of angiogenic, chondrogenic and osteogenic activity. Clinical evidence confirms that US can effectively treat delayed unions and non-unions.

US therapy applied to fracture healing relates to differential energy absorption of ultrasound that gives rise to an acoustic streaming, and resultant fluid flow as a mechano-transduction signal. Low energy mechanical stimulation, e.g. low intensity pulsed ultrasound (LIPUS), accelerates healing of bone fractures and other recovery. See, U.S. Patent Publication 2008/0021327 A1 of Ahmed El-Bialy, the contents of which are incorporated herein by reference. LIPUS stimulation transmits mechanical energy through and into biological tissues as an acoustic pressure wave and has been widely used in medicine as a non-invasive therapeutic tool, showing an accelerated rate of healing of fresh fractures.

LIPUS stimulation can assist non-union and accelerate fracture repair. However, the effectiveness of localized LIPUS with optimized intensity has not been fully investigated. Moreover, soft tissue and cortical shell interference limits use of LIPUS stimulation.

LIPUS is a biophysical form of intervention in the fracture-repair process, which through several mechanisms accelerates healing of fresh fractures and enhances callus formation in delayed union and nonunion. The acoustic pressure wave induced by US is indicative of a mechanical signal that takes full advantage of bone tissue sensitivity to low-level physical signals. However, such acoustically driven mechanical signal is several orders of magnitude lower than the peak strains generated by functional load-bearing, while the rates of loading induced by the US are several orders of magnitude higher. Extremely low-level, high-frequency mechanical signals persist in functionally loaded bone and represent strong regulatory signals to skeletal tissue, even during fracture-healing.

Therapeutic US, and some operative US, uses intensities as high as 1 to 30 W/cm$^2$ and can cause considerable heating in living tissues. The use of US as a surgical instrument involves even higher levels of intensity (5 to 300 W/cm$^2$), and sharp bursts of energy used to fragment calculi initiate the healing of non-unions, ablate diseased tissues such as cataracts, and even remove methylmethacrylate cement during revision of prosthetic joints. The intensity level used for imaging, which is five orders of magnitude below that used for surgery, is regarded as non-thermal and nondestructive. Current therapeutic US uses plane waves and exposes the energy to broad range of tissues. The radical changes in density inherent in a healing callus may lose significant amounts of energy in the pathway of ultrasound. A localized and targeted/guided exposure of LIPUS overcomes these limitations and dramatically increases the efficiency of the treatment. The combined diagnostic and therapeutic quantitative ultrasound (QUS) with focal scan as in the present invention overcomes such shortcomings.

In the present invention, focused LIPUS of modified LIPUS (mLIPUS) acts as an alternating pressure wave, creating localized pressure gradients within micro porosities of the subject bone, and anabolic shear forces on cell membranes, thereby changing local solute concentrations and initiating local fluid flow exchange/interaction. In vitro studies show that mLIPUS enhances osteoblast proliferation and endochondral bone formation and in vivo studies show mLIPUS to be anabolic in fresh fractures, enhancing endochondral bone formation, mineral density and mechanical strength.

The present invention combines ultrasound focusing and mLIPUS stimulation to provide early identification of bone disorder and accelerate localized fracture healing.

SUMMARY OF THE INVENTION

Accordingly, the present invention solves the above-mentioned problems of conventional systems, and provides an apparatus and method that combines ultrasound focusing and mLIPUS stimulation for early prediction of bone disorder and guided acceleration of fracture healing, using scanning confocal acoustic imaging and a modified low-intensity pulse ultrasound.

In the present invention, a method and apparatus are provided for non-invasive bone fracture detection and accelerated healing. A paired phased array ultrasound scanning apparatus with multi-element transducers simultaneously maps three-dimensional bone surface topology at opposite surfaces along an ultrasound wave pathway. The mapped three dimensional topology is utilized to measure a thickness of the mapped bone and to detect a region of interest having a bone deterioration or a bone fracture. US wave velocity and attenuation are calculated as the ultrasound wave passes through the detected region of interest and a LIPUS pulse is applied to the region of interest, with the paired phased array ultrasound scanning apparatus focusing application of the LIPUS pulse.

BRIEF DESCRIPTION OF THE DRAWINGS

The above and other objects, features and advantages of certain exemplary embodiments of the present invention will be more apparent from the following detailed description taken in conjunction with the accompanying drawings, in which.

DETAILED DESCRIPTION OF THE PREFERRED EMBODIMENTS

Figure 1:
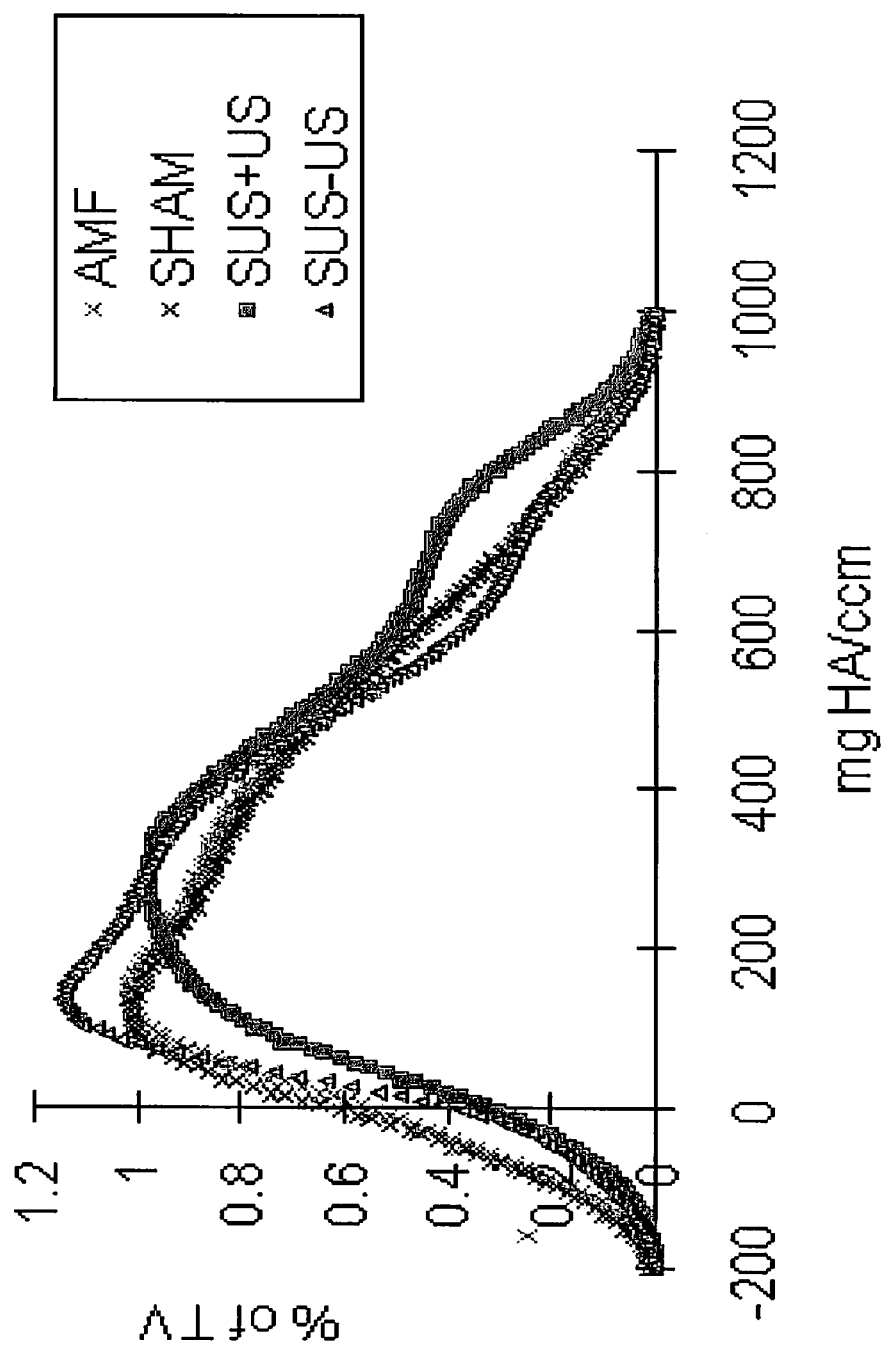
FIG. 1 is a chart showing mineral density distribution of the callus.

The following detailed description of preferred embodiments of the invention will be made in reference to the accompanying drawings. In the following description, explanation of related functions or constructions known in the art are omitted for the sake of clarity in understanding the concept of the invention that would otherwise obscure the invention with unnecessary detail.

Scanning confocal acoustic diagnostic (SCAD) is utilized to detect regions of interest (ROI) for identification of bone deterioration and fracture. A low intensity pulse ultrasound (LIPUS) device is implemented within the diagnostic SCAD, to provide localized treatment upon identification of a bone defect region. The LIPUS guided by the SCAD. Enhanced local treatment using LIPUS device is obtained by combining the SCAD and LIPUS transducers. Focused ultrasound transducers for therapeutic use at the SCAD guided bone deterioration location preferably operate in a frequency range of 0.5-1.5 MHz.

In the present invention, an mLIPUS oscillatory force is applied in a focal region, to elevate the tissue therapy US level. The thermal application includes cavitations, radiation force, microstreaming and dynamic shear force, wherein a particle, such as a cell, within the focal region experiences transfer of momentum from the US wave. A US wavelength close to medium particle size, such as osteoblasts, osteoclasts, and osteocytes, generates local pressure wave gradients and initiates oscillatory fluid flow in the focal region exposed to the US wave. Dynamic acoustic radiation force resulting from an intensity-modulated focused transducer and frequency mediated pressure gradient is optimized using deformation measurements.

In preferred embodiments of the present invention, mLIPUS is applied at 1.5 MHz, 1.45 MHz, or dual frequency combinations having a frequency difference of approximately 0.01–0.05 MHz, and modulated at combinations of 1.5 MHz and 1.45 MHz. The repetition frequency is preferably applied at steps of 0.5 kHz, 1 kHz, 1.25 kHz, 1.5 kHz and 2.25 kHz, to control overall acoustic energy under 100 mW/cm² while optimizing effective energy at the treated region. Thus, mLIPUS effectively mediates the local fluid acoustic streaming and fluid flow, as well as velocity gradients. The velocity and the velocity rate are used to calculate shear force, providing an expected mLIPUS optimized shear force in a range of 0.1-10 dyn/cm², for bone cell activation.

To overcome hurdles that include soft tissue and cortical shell interference, improved qualitative US is obtained by utilizing an image based SCAD system that increases the resolution, sensitivity, and accuracy in diagnosing osteoporosis through confocal acoustics to improve signal/noise ratio, and through extracting surface topology to accurately calculate UV. The image based SCAD system minimizes the scanning time while maintaining resolution via micro-processor controlled and phased array electronic confocal scanning, e.g., in deep bone tissue scan, and increases BUA accuracy by incorporating cortical shell attenuation in ROI. The image based SCAD system validates structural and strength properties using micro-CT, nano-identification and mechanical testing; predicts local trabecular bulk stiffness and microstructure of bone; and generates a physical relationship between UT parameters and bone quality. The image based SCAD system, combined with the LIPUS device, provides guided US treatment for early, accelerated fracture healing.

In the present invention, a combined LIPUS/SCAD system provides focused therapeutic US at an identified defect region for nondestructive treatment of osteopenia and fracture. The SCAD generates acoustic images in a region of interest in the skeleton, including cortical and trabecular bone, provides guided treatment, and monitors longitudinal healing process. The invention targets critical skeletal sites that are significantly affected by disuse osteopenia and potentially at risk of fracture, i.e., hip, spine and wrist regions.

In a preferred embodiment, US transducers are combined in the diagnostic mode of the SCAD with focused LIPUS US transducers for guided therapeutic application in a detected region of interest of bone deterioration. The transmitted US is preferably configured at characteristic frequencies of 0.5-1.5 MHz. The US transducer is preferably constructed with piezoelectric traducers sandwiched between layers of gold, and the focus lens was made by silicon composite material for better water coupling for tissue and ultrasound. The transducers are preferably designed to a constant focus length of 20-150 mm for multiple scan sites.

The LIPUS is preferably controlled at 30-60 mW/cm², comparable to diagnostic US intensities used in sonogram (fetal monitoring) procedures. However, since the LIPUS is applied in a guided mode with SCAD, the US energy is directly targeted to the ROI and performs an effective treatment. The combined diagnostic unit is, in a preferred embodiment, provided in a portable treatment unit with the specifications set out in Table 1.

TABLE 1

| | |
|---|---|
| Modulating signal burst width | 200 ± 10% microsecond (us) |
| Repetition rate | 1.0 ± 10% kilohertz (kHz) |
| Effective radiating area | 3.88 ± 1% square cm (cm²) |
| Temporal average power | 117 ± 30% milliwatts (mW) |
| Temporal maximum power | 625 ± 30% milliwatts (mW) |
| Peak power | 1.25 ± 30% watts |
| Spatial avg.-temporal avg. (SATA) | 30-60 ± 30% mW/cm² |
| Spatial avg.-temporal maximum (SATM) | 161 ± 30% mW/cm² |
| Beam non-uniformity ratio (BNR) | 4.0 maximum |

Rat model fracture healing was utilized to evaluate the accelerating fracture healing of another preferred embodiment of the present invention. In the rat model, evaluation was performed on eighteen animals divided into four groups, under disuse conditions using hind-limb suspension (HLS), with standard fractures performed at a left femur and K-Wire applied to the femur from a knee condyle. The first two groups include an age match fracture (AMF) without HLS, with the group one receiving US treatment with signal output, AMF (n–5), and the second group receiving sham ultrasound control, without signal output (n=5). Groups three and four included hind limb suspension with femur fracture, with group three receiving US treatment, HLS+LIPUS (n=4) and group four not receiving US treatment, HLS only (n=4). Results obtained from the groups are shown in FIGS. 1 and 2.

On the following day, LIPUS was applied to all groups at 1.5 MHz, 1 KHz pulsed, a 20% duty cycle, and 30 mW/cm² intensity, SATA, for 20 minutes a day, five days a week, for a total of three weeks. Two percent isoflurane anesthesia is given to those groups when treated with ultrasound, as well as to the sham control group. At one-week intervals, X-rays were taken of the fractured femur for tracking of the healing procedure.

After the third week, bone samples were harvested and the K-wire carefully removed from the femur, the callus density and quality was examined with microCT scan (SCANCO uCT40) in the resolution of 18 um, 5 mm (278 slices), covering the callus region. The protocol is able to calculate newly mineralized callus within the contour lines.

Figure 2:
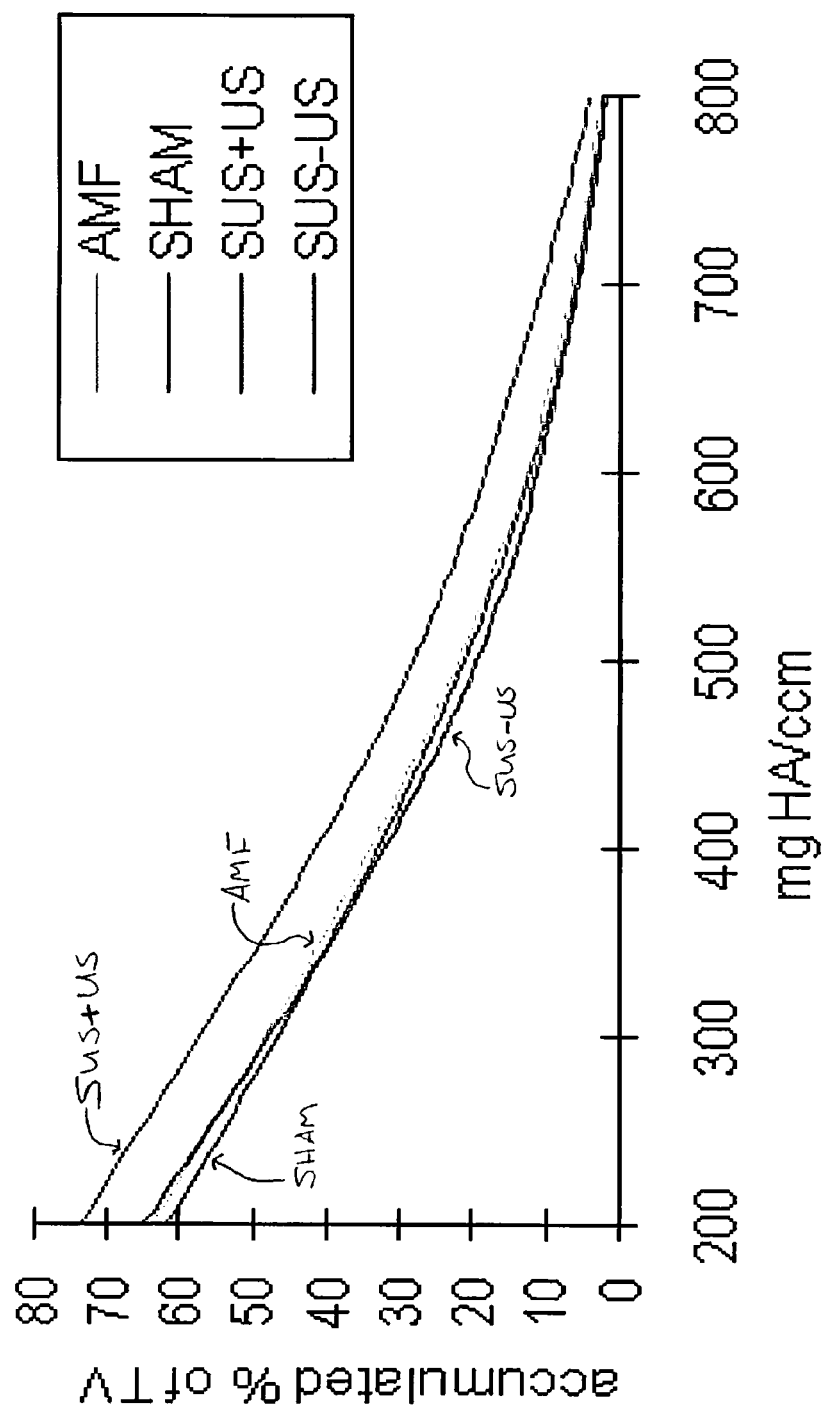
FIG. 2 is a chart showing accumulated callus mineralization above a threshold density.

The callus mineralization distribution shown in FIG. 1 exhibits in group three, i.e. the suspended rats treated with ultrasound, a small peak distribution between 750 and 800 mg HA/ccm points, indicating a callus mineralization much higher than the other three groups, as shown in FIG. 2. The other three groups, however, did not display a significant difference between each other, other than group four, the suspended rats without ultrasound treatment, showing slightly less mineralization area around 600 mg HA/ccm point, making group four the lowest in high mineralization area (>400 mg HA/ccm), compared to other groups, as shown in FIG. 2.

CT scan settings of 0.8, 1, 250 were chosen and applied to each callus, to threshold the CT pictures, and the average BV/TV as well as the standard deviation of each group is abstained and compared, listed in Table 2. The SHAM control group data was used as the baseline to calculate the difference change percentages after three weeks.

TABLE 2

| Groups | Threshold | BV/TV | STDEV | % change |
|---|---|---|---|---|
| AMF | 250 | 0.4404 | 0.066 | 3.94% |
| SHAM | 250 | 0.4237 | 0.124 | 0.00% |
| SUS+US | 250 | 0.5266 | 0.080 | 24.27% |
| SUS−US | 250 | 0.4314 | 0.108 | 1.82% |

As shown and described above, the hind limb suspension group with ultrasound treatment developed superior callus mineralization quality, over 20% better than the other groups, and the suspended group without ultrasound treatment exhibited the worst bone mineralization among the groups, showing that the US treatment promoted bone mineralization. For the two unsuspended groups without ultrasound treatment, development of callus mineralization was mostly similar, which is not unreasonable since a three weeks recovery after fracture is shorter than normally required for broken bone recovery in rats.

While the invention has been shown and described with reference to certain exemplary embodiments of the present invention thereof, it will be understood by those skilled in the art that various changes in form and details may be made therein without departing from the spirit and scope of the present invention as defined by the appended claims and equivalents thereof.

What is claimed is:

1. An apparatus for application of a guided and focused ultrasound for treatment, said apparatus comprising:
    a scanning confocal acoustic diagnostic (SCAD) apparatus configured to identify a region of interest having a bone deterioration or bone detection in a target employing multi-element transducers; and
    a low intensity pulse ultrasound (LIPUS) device configured to apply a focused therapeutic ultrasound at said identified region of interest employing LIPUS transducers configured to focus emitted ultrasound,
    wherein said SCAD apparatus controls and guides said LIPUS device in a guided mode to focus, and directly target, ultrasonic energy in said focused therapeutic ultrasound at said identified region of interest for effective treatment.

2. The apparatus of claim 1, wherein an enhanced local treatment of said identified region of interest is provided by combining ultrasounds from said multi-element transducers and said LIPUS transducers.

3. The apparatus of claim 2, wherein said LIPUS device localizes said ultrasonic energy at said region of interest during said guided mode.

4. The apparatus of claim 1, wherein said SCAD apparatus is configured to predict local trabecular bulk stiffness and microstructure of bone.

5. The apparatus of claim 1, wherein said LIPUS device is configured to apply said focused therapeutic ultrasound at a characteristic frequency selected from a range from 0.5 MHz to 1.5 MHz.

6. The apparatus of claim 1, wherein said SCAD apparatus comprises a paired phased array ultrasound scanning apparatus.

7. The apparatus of claim 6, wherein said paired phased array ultrasound scanning apparatus focuses application of said focused therapeutic ultrasound.

8. The apparatus of claim 1, wherein said LIPUS transducers are combined with said multi-element transducers during said applying of said focused therapeutic ultrasound.

9. The apparatus of claim 1, wherein said LIPUS transducers are configured to apply ultrasound at a combination of dual frequencies having a frequency difference in a range from 0.01 MHz to 0.05 MHz.

10. A method of applying a focused ultrasound for treatment, said method comprising:
    identifying a region of interest having a bone deterioration or bone detection in a target employing a scanning confocal acoustic diagnostic (SCAD) apparatus that employs multi-element transducers; and
    applying a focused therapeutic ultrasound employing a low intensity pulse ultrasound (LIPUS) device at said identified region of interest comprising LIPUS transducers configured to focus emitted ultrasound, wherein said SCAD apparatus controls said LIPUS device in a guided mode to focus, and directly target, ultrasonic energy in said focused therapeutic ultrasound at said region of interest for effective treatment.

11. The method of claim 10, wherein an enhanced local treatment of said identified region of interest is provided by combining ultrasounds from said multi-element transducers and said LIPUS transducers.

12. The method of claim 11, wherein said LIPUS device localizes said ultrasonic energy at said region of interest during said guided mode.

13. The method of claim 10, further comprising predicting local trabecular bulk stiffness and microstructure of bone of said target employing said SCAD apparatus.

14. The method of claim 10, wherein said focused therapeutic ultrasound is applied at a characteristic frequency selected from a range from 0.5 MHz to 1.5 MHz.

15. The method of claim 10, wherein said SCAD apparatus comprises a paired phased array ultrasound scanning apparatus.

16. The method of claim 15, wherein said paired phased array ultrasound scanning apparatus focuses application of said focused therapeutic ultrasound.

17. The method of claim 10, wherein said LIPUS transducers are combined with said multi-element transducers during said applying of said focused therapeutic ultrasound.

18. The method of claim 10, wherein said LIPUS transducers apply ultrasound at a combination of dual frequencies having a frequency difference in a range from 0.01 MHz to 0.05 MHz.

* * * * *